(12) United States Patent
Bhat et al.

(10) Patent No.: US 9,808,443 B1
(45) Date of Patent: Nov. 7, 2017

(54) CYCLOOXYGENASE INHIBITORS

(71) Applicant: KING SAUD UNIVERSITY, Riyadh (SA)

(72) Inventors: Mashooq Ahmad Bhat, Riyadh (SA); Mohamed A. Al-Omar, Riyadh (SA); Mohammad Raish, Riyadh (SA); Mushtaq Ahmad Ansari, Riyadh (SA); Hatem A. Abuelizz, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/362,733

(22) Filed: Nov. 28, 2016

(51) Int. Cl.
*A61K 31/404* (2006.01)
*C07D 209/18* (2006.01)

(52) U.S. Cl.
CPC .......... *A61K 31/404* (2013.01); *C07D 209/18* (2013.01)

(58) Field of Classification Search
CPC .............................. A61K 31/404; C07D 209/18
USPC ......................................................... 548/400
See application file for complete search history.

(56) References Cited

U.S. PATENT DOCUMENTS

| 6,277,878 | B1 | 8/2001 | Nakao et al. |
| 6,300,363 | B1 | 10/2001 | Stevens et al. |
| 6,303,628 | B1 | 10/2001 | Nakao et al. |
| 6,608,070 | B1 | 8/2003 | Nakao et al. |
| 2015/0328216 | A1 | 11/2015 | Penthala et al. |

FOREIGN PATENT DOCUMENTS

CN 103622969 A 3/2014

*Primary Examiner* — Kristin Vajda
(74) *Attorney, Agent, or Firm* — Richard C. Litman

(57) ABSTRACT

Cyclooxygenase inhibitors include compounds of the formula:

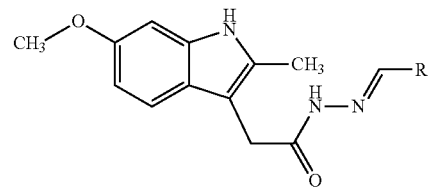

where R represents phenyl, nitrophenyl, 2-nitrophenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, dimethylaminophenyl, 3-methoxyphenyl, 4-ethoxyphenyl, 2,4,5-trimethoxyphenyl, 3,4,5-trimethoxyphenyl, 2,4,6-trimethoxyphenyl, and 2,4-dimethoxyphenyl, 3-hydroxyphenyl, 4-dimethylaminophenyl, or 2,3,4-trimethoxyphenyl.

7 Claims, 7 Drawing Sheets

Table 1. Anti-inflammatory activity of compounds (S1-S18).

| Treatments | Increase in Paw Volume | | % Inhibition | | Potency |
|---|---|---|---|---|---|
| | After 2 hours | After 3 hours | After 2 hours | After 3 hours | |
| S1 | 0.53±0.04** | 0.53±0.04*** | 43.95 | 44.31 | 0.57 |
| S2 | 0.81±0.03* | 0.79±0.02*** | 14.71 | 17.93 | 0.21 |
| S3 | 0.36±0.04*** | 0.37±0.04*** | 61.99 | 61.20 | 0.79 |
| S4 | 0.43±0.01*** | 0.43±0.02*** | 54.46 | 55 | 0.71 |
| S5 | 0.82±0.07 | 0.85±0.06 | 13.48 | 11.89 | 0.16 |
| S6 | 0.46±0.04*** | 0.46±0.05*** | 51.31 | 51.89 | 0.66 |
| S7 | 0.36±0.02*** | 0.36±02*** | 61.47 | 62.24 | 0.80 |
| S8 | 0.91±0.04 | 0.95±0.03 | 4.20 | 0 | 0.02 |
| S9 | 0.57±0.02*** | 0.51±0.03*** | 39.40 | 46.37 | 0.55 |
| S10 | 0.68±0.02*** | 0.69±0.01*** | 28.19 | 27.75 | 0.36 |
| S11 | 0.45±0.02*** | 0.43±0.03*** | 52.18 | 55 | 0.69 |
| S12 | 0.81±0.03* | 0.79±0.03** | 14.71 | 18.27 | 0.21 |
| S13 | 0.76±0.33** | 0.82±0.04* | 19.96 | 14.65 | 0.22 |
| S14 | 0.35±0.02*** | 0.34±0.02*** | 62.69 | 63.69 | 0.82 |
| S15 | 0.88±0.01 | 0.89±0.09 | 7.35 | 7.06 | 0.09 |
| S16 | 0.78±0.04* | 0.79±0.04* | 17.68 | 17.41 | 0.22 |
| S17 | 0.49±0.02*** | 0.48±0.02*** | 47.81 | 50.34 | 0.63 |
| S18 | 0.69±0.12 | 0.62±0.05*** | 27.49 | 35.68 | 0.40 |
| Indomethacin | 0.20±0.02*** | 0.22±0.02*** | 77.23 | 76.89 | 1.00 |
| Control | 0.95±0.02 | 0.96±0.02 | - | - | - |

All values represent mean ± SEM.*$p<0.05$, $<0.01$, *$p<0.001$; ANOVA, followed by Dunnett's multiple comparison test.(n-6) All data were compared with control group.

*FIG. 2*

Table 2. Analgesic activities of selected compounds.

| Treatments | Pretreatment (0 hour) Mean ±SE (Second) | Post treatment (3 hours) Mean ±SE (Second) | %Inhibition | Potency |
|---|---|---|---|---|
| S1 | 8.33±0.49 | 10.83±0.79* | 30 | 0.35 |
| S3 | 7.33±0.42 | 11.83±0.65*** | 61.36 | 0.72 |
| S4 | 6.83±0.30 | 7.33±0.40 | 7.31 | 0.08 |
| S6 | 7.33±0.33 | 8.33±0.49 | 13.63 | 0.16 |
| S7 | 7.33±0.42 | 10.83±0.47*** | 47.72 | 0.56 |
| S9 | 7.16±0.30 | 11.16±0.60*** | 55.81 | 0.66 |
| S10 | 6.66±0.33 | 10.83±0.47*** | 62.50 | 0.74 |
| S11 | 7.16±0.47 | 10.16±0.65** | 41.86 | 0.49 |
| S14 | 6.16±0.30 | 10.50±0.42*** | 70.27 | 0.83 |
| S17 | 6.50±0.22 | 10.50±0.42*** | 61.53 | 0.73 |
| S18 | 6.16±0.30 | 7.66±0.33** | 24.32 | 0.28 |
| Indomethacin | 7.33±0.42 | 13.50±0.42*** | 84.09 | 1.00 |

All values represent mean ± SEM.*p<0.05, <0.01, *p<0.001; ANOVA, followed by Dunnett's multiple comparison test, (n-6). All data were compared with control group.

*FIG. 3*

Table 3. Ulcerogenic and Lipid Peroxidation Activity of Compounds (S1-18) in liver and kidney tissue

| Treatments | Ulcerogenic activity (Index) Mean ±SE | % Inhibition | Nanomoles of MDA content (Liver tissue) Mean ±SEM/100mg tissue | % Change | Nanomoles of MDA content (Kidney tissue) Mean ±SEM/100mg tissue | % Change |
|---|---|---|---|---|---|---|
| S1 | 0.582±0.17 | 38.6 | 7.00±0.25* | 14.13 | 4.78±0.14*** | 28.66 |
| S2 | 0.362±0.17 | 61.81 | 5.94±0.25*** | 27.22 | 5.89±0.14** | 12.10 |
| S3 | 0.116±0.07** | 87.76 | 5.55±0.18*** | 31.93 | 6.83±0.17 | 1.91 |
| S4 | 0.00 | 100 | 4.70±5.75*** | 40.32 | 4.01±0.14*** | 40.12 |
| S5 | 0.532±0.08 | 43.88 | 6.08±0.18*** | 18.84 | 4.40±0.27*** | 40.12 |
| S6 | 0.00 | 100 | 4.35±0.16*** | 45.59 | 3.80±0.12*** | 43.31 |
| S7 | 0.432±0.04* | 54.30 | 6.32±0.14*** | 22.51 | 5.64±0.20** | 15.92 |
| S8 | 0.132±0.08** | 86.07 | 6.88±0.37* | 15.70 | 5.94±0.18* | 11.46 |
| S9 | 0.064±0.03** | 93.24 | 7.82±0.28 | 4.18 | 6.02±0.19* | 10.19 |
| S10 | 0.948±0.17 | 0 | 8.58±0.38 | 5.23 | 7.17±0.20 | 7.00 |
| S11 | 0.00 | 100 | 4.74±0.28*** | 41.88 | 4.14±0.18*** | 38.21 |
| S12 | 0.316±0.09* | 66.66 | 5.85±0.18*** | 28.27 | 5.29±0.28** | 21.09 |
| S13 | 0.696±0.09 | 26.58 | 5.29±0.17*** | 35.07 | 5.12±0.16*** | 23.56 |
| S14 | 0.616±0.11 | 35.2 | 5.59±0.19*** | 41.36 | 5.68±0.12** | 15.28 |
| S15 | 0.00 | 100 | 4.78±0.06*** | 41.36 | 4.01±0.23*** | 40.12 |
| S16 | 0.966±0.16 | 0 | 7.56±0.43 | 7.32 | 7.17±0.22 | 7.00 |
| S17 | 0.00 | 100 | 4.65±0.21*** | 42.93 | 4.44±0.17*** | 33.75 |
| S18 | 0.598±0.11 | 36.91 | 5.81±0.41*** | 28.79 | 5.64±0.18** | 15.92 |
| Indomethacin | 0.948±0.21 | 0 | 8.16±0.28*** | 114.60 | 6.70±0.20*** | 98.73 |
| Control | 0.00 | 100 | 3.80±0.18 | - | 3.37±0.12 | |

Values represent mean ± SEM. *p<0.05, <0.01, *p<0.001; ANOVA, followed by Dunnett's multiple comparison test.(n-6). All data were compared with indomethacin group.

FIG. 4

CYCLOOXYGENASE INHIBITORS

BACKGROUND OF THE INVENTION

1. Field of the Invention

The present invention relates to cyclooxygenase inhibitors, and particularly to 2-(5-methoxy-2-methyl-1-indol-3yl)-N-[(E)-substituted phenyl methylidine] aceto hydrazide derivatives.

2. Description of the Related Art

Conversion of arachidonic acid to prostaglandin $H_2$ ($PGH_2$) is catalyzed by the cyclooxygenase (COX) enzyme. Because the prostaglandin $H_2$ is an unstable intermediate, it is converted to many prostanoids by specific isomerase enzymes. This process of biosynthesis occurs in all tissues of the human body. Pain and fever associated with inflammation are the non-beneficial effects of prostaglandins, while gastro-intestinal protection and platelet function are among their beneficial effects. The COX enzyme has two isoforms, COX-1 and COX-2, which are each regulated differently. COX-1 provides cytoprotection in the gastrointestinal (GI) tract and COX-2 mediates inflammation.

Nonsteroidal anti-inflammatory drugs (NSAIDs) are effective analgesics frequently used in palliative care. However, these medicines are related with numerous adverse side effects that are largely due to gastrointestinal toxicity, with subsequent complications, such as gastroduodenal perforations, ulcers and bleeds. Such toxicity is typically ascribed to the inhibition of cyclooxygenase-1 (COX-1). Thus, selective inhibitors of cyclooxygenase-2 (COX-2) were developed in an attempt to reduce these side effects. Trial studies to date confirm that these drugs do indeed have a reduced incidence of gastro-duodenal toxicity. Prior to the introduction of the COX-2 selective inhibitors, patients at high risk were often prescribed a gastro-protective agent (such as misoprostol or a proton pump inhibitor) with a conventional NSAID.

Most of the common nonsteroidal anti-inflammatory drugs (NSAIDs) show a greater selectivity for COX-1 than COX-2. Thus, long term use of NSAIDS may produce gastric irritation, bleeding and ulceration. It is assumed that inhibition of COX-2 selectively would result in the same anti-inflammatory benefits that non-selective NSAIDs provide but with fewer incidences of gastrointestinal side effects. COX-2 inhibitors provide synthesis of cytoprotection prostaglandins, reducing ulceration and bleeding, however COX-2 inhibitors have also been found to have cardiovascular side effects.

Indomethacin is an indole acetic acid derivative NSAID known to induce ulceration. Chemical modifications have improved the safety profile of various NSAIDs, thus showing the possibility for synthetic modifications to result in an increased anti-inflammatory activity with reduced ulcerogenicity. It would be desirable to provide an indole derivative having the anti-inflammatory and analgesic properties of a COX-2 inhibitor NSAID, but which also provides gastric sparing activity.

Thus, a COX-2 inhibitor solving the aforementioned problems are desired.

SUMMARY OF THE INVENTION

Cyclooxygenase inhibitors include compounds of the formula:

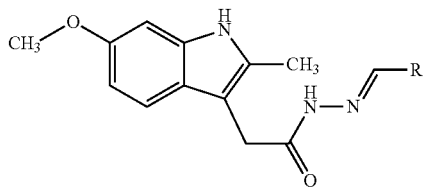

where R represents phenyl, nitrophenyl, 2-nitrophenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, dimethylaminophenyl, 3-methoxyphenyl, 4-ethoxyphenyl, 2,4,5-trimethoxyphenyl, 3,4,5-trimethoxyphenyl, 2,4,6-trimethoxyphenyl, and 2,4-dimethoxyphenyl, 3-hydroxyphenyl, 4-dimethylaminophenyl, or 2,3,4-trimethoxyphenyl.

These and other features of the present invention will become readily apparent upon further review of the following specification.

BRIEF DESCRIPTION OF THE DRAWINGS

FIG. 2 is a table providing levels of anti-inflammatory activity of the cyclooxygenase inhibitor compounds (S1-S18) prepared according to the present invention.

FIG. 3 is a table providing levels of analgesic activity of the cyclooxygenase inhibitor compounds (S1-S18) prepared according to the present invention.

FIG. 4 is a table providing levels of ulcerogenic and lipid peroxidation activity of the cyclooxygenase inhibitor compounds (S1-S18) prepared according to the present invention.

Similar reference characters denote corresponding features consistently throughout the attached drawings.

DETAILED DESCRIPTION OF THE PREFERRED EMBODIMENTS

Figure 1:
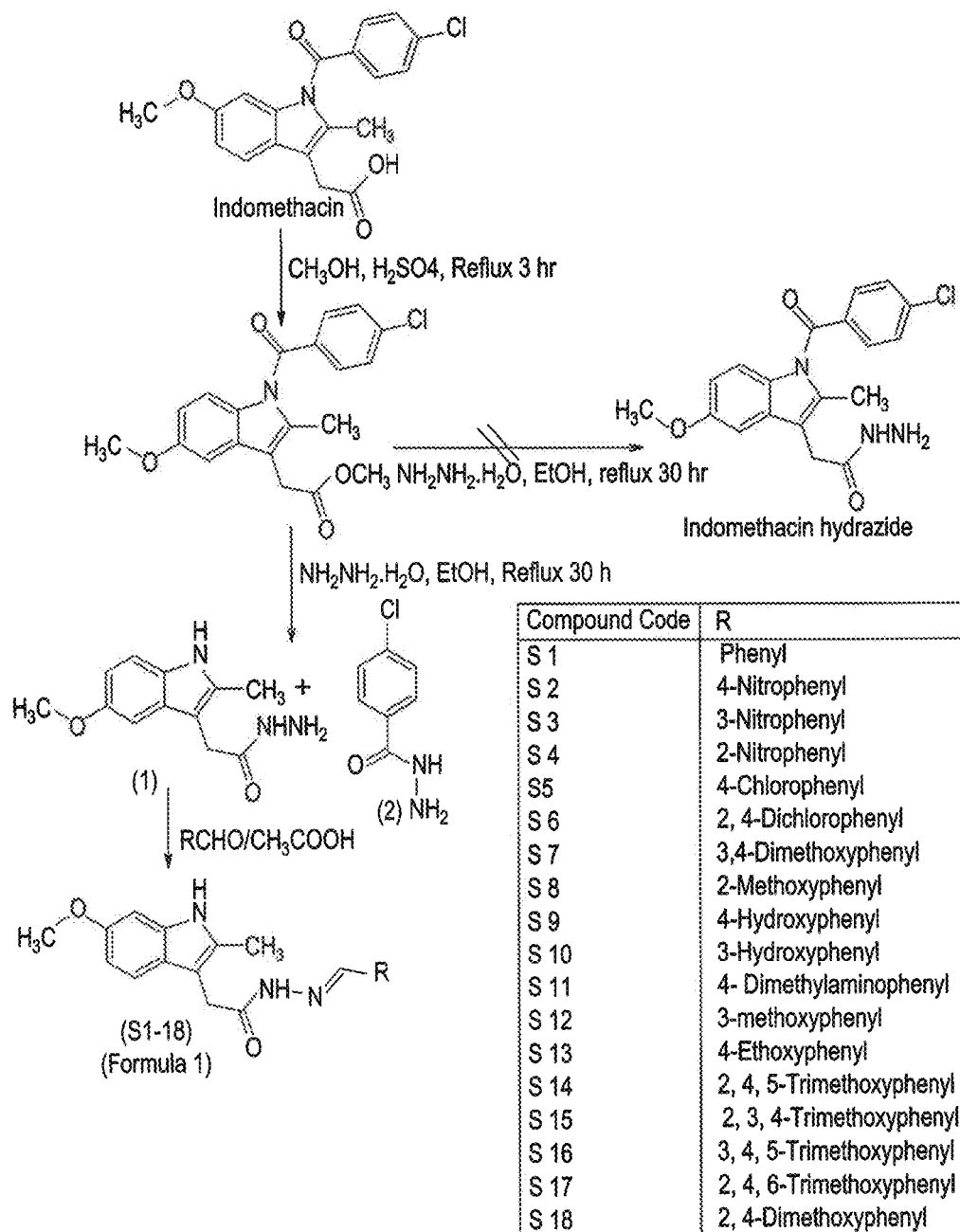
FIG. 1 illustrates the synthesis of cyclooxygenase inhibitors according to the present invention.

Cyclooxygenase inhibitors include compounds of the formula:

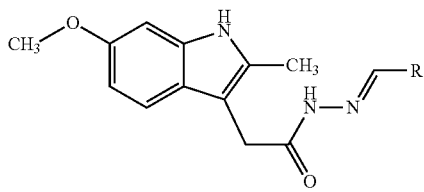

where R represents phenyl, nitrophenyl, 2-nitrophenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, dimethylaminophenyl, 3-methoxyphenyl, 4-ethoxyphenyl, 2,4,5-trimethoxyphenyl, 3,4,5-trimethoxyphenyl, 2,4,6-trimethoxyphenyl, and 2,4-dimethoxyphenyl, 3-hydroxyphenyl, 4-dimethylaminophenyl, or 2,3,4-trimethoxyphenyl. The cyclooxygenase inhibitor can be synthesized by refluxing indol hydrazide with appropriate substituted benzaldehydes in the presence of ethanol and catalytic amounts of glacial acetic acid, as described in detail herein.

The cyclooxygenase inhibitors can include 2-(5-methoxy-2-methyl-1-indol-3yl)-N-[(E)-substituted phenyl methylidine] aceto hydrazide derivatives or a pharmaceutically acceptable salt thereof. The cyclooxygenase inhibitors can be used as an active ingredient of pharmaceuticals for treating inflammation or inflammatory diseases. The cyclooxygenase inhibitors can be used as analgesic and/or gastric sparing agents. The cyclooxygenase inhibitors can be potent inhibitors of cyclooxygenase-2 (COX-2 inhibitors).

A pharmaceutically acceptable salt includes any non-toxic salt of the present cyclooxygenase inhibitors, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mutate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

It should be understood that the present cyclooxygenase inhibitors may be administered to a subject by any suitable route. For example, the cyclooxygenase inhibitors can be administered orally (including bucally and sublingually), nasally, rectally, parenterally, intracisternally, intra vaginally, intraperitoneally, topically and transdermally (as by powders, ointments, or drops). The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation is also contemplated, including, for example, embedding an indole derivative composition according to the present invention in the body such as, for example, in a tissue, in the abdominal cavity, under the splenic capsule, brain, or in the cornea. Accordingly, the route of administration can include intranasal administration, oral administration, inhalation administration, subcutaneous administration, transdermal administration, intradermal administration, intra-arterial administration, with or without occlusion, intracranial administration, intraventricular administration, intravenous administration, buccal administration, intraperitoneal administration, intraocular administration, intramuscular administration, implantation administration, topical administration, intra-tumor administration and/or central venous administration.

It should be understood that the cyclooxygenase inhibitors may be manufactured as, or incorporated into, pharmaceutical compositions including one or more of the cyclooxygenase inhibitors or pharmaceutically equivalent salts thereof. The cyclooxygenase inhibitors may be intimately admixed with a pharmaceutically acceptable carrier according to conventional pharmaceutical compounding techniques. Carriers, as used herein, are inert pharmaceutical excipients, including, but not limited to, binders, suspending agents, lubricants, flavorings, sweeteners, preservatives, dyes, and coatings. In preparing compositions in oral dosage form, any suitable type of pharmaceutical carrier may be employed. For example, for liquid oral preparations, suitable carriers and additives include water, glycols, oils, alcohols, flavoring agents, preservatives, coloring agents and the like; and for solid oral preparations, suitable carriers and additives include starches, sugars, diluents, granulating agents, lubricants, binders, disintegrating agents and the like. For parenteral use, the carrier is typically sterile water, although other ingredients, for example, for purposes such as aiding solubility or for preservation, may be included. Injectable suspensions may also be prepared, in which case appropriate liquid carriers, suspending agents and the like may be employed. For example, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

As a further alternative, the cyclooxygenase inhibitors may be administered in the form of liposomes. Liposomes generally are derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients and the like. Exemplary lipids include phospholipids and the phosphatidyl cholines (lecithins), both natural and synthetic.

Pharmaceutical compositions for parenteral injection can include pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

It should be further understood that the present compositions may include adjuvants, such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents, such as sugars, sodium chloride and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be provided in unit dosage forms, such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound is mixed under sterile conditions with a pharmaceutically acceptable carrier and any needed preservatives, buffers, or propellants which may be required. Ophthalmic formulations, eye ointments, powders, and solutions are also are contemplated. The composition can be presented in a form suitable for daily, weekly or monthly administration. The pharmaceutical compositions will contain, per dosage unit, e.g., tablet, capsule, powder, injection, teaspoonful, suppository and the like, an amount of the active ingredient necessary to deliver an effective dose. A therapeutically effective amount of the cyclooxygenase inhibitor or an amount effective to treat inflammation may be determined initially from in vivo assays described herein and adjusted for specific desired cyclooxygenase inhibitors using routine methods.

FIG. 1 illustrates the synthesis of the 2-(5-methoxy-2-methyl-1-indol-3yl)-N-[(E)-substituted phenyl methylidine] aceto hydrazide derivatives (labeled as Formula 1 in FIG. 1). The hydrazide, 2-(6-methoxy-2-methyl-1H-indol-3-yl)-acetohydrazide, was synthesized by refluxing methyl ester of indomethacin and hydrazine hydrate in presence of absolute ethanol. The hydrazide was refluxed with a selected substituted benzaldehyde in the presence of ethanol and a catalytic amount of glacial acetic acid. As shown in FIG. 1, 18 different cyclooxygenase inhibitor compounds (S1-S18) were made. The structures of all synthesized compounds were assigned on the basis of elemental analysis as well as FT IR, $^1$H NMR, $^{13}$C NMR and mass spectral data.

The methyl ester of indomethacin (0.01 mol) and hydrazine hydrate (99%) (0.2 mol) were refluxed in absolute ethanol (50 mL) for 30 hours. The mixture was concentrated, cooled and poured in crushed ice in small portions while stirring, and kept for 3-4 hours at room temperature. The solid separated out was filtered, dried and crystallized from ethanol. The product was carefully checked by thin layer chromatography, and two compounds were isolated by column chromatography by using different fractions of n-hexane and ethyl acetate. The first compound was 2-(6-methoxy-2-methyl-1H-indol-3-yl) acetohydrazide (Compound 1), and was obtained as the major product. The second compound, a minor product, was 4-chlorobenzohydrazide (Compound 2). Both compounds were fully characterized by the spectral data and are further described below.

Data obtained for 2-(6-methoxy-2-methyl-1H-indol-3-yl) acetohydrazide (Compound 1) are as follows: Color: white; Yield: 70%; M.p.: 168-170° C.; UV λ max (Methanol)=280 nm; $^1$H NMR (500 MHz, DMSO-$d_6$): δ=2.38 (3H, s, $CH_3$), 3.54 (2H, s, $CH_2$), 3.80 (3H, s, $OCH_3$), 4.26 (2H, s, $NH_2$, $D_2O$ exchg.), 6.67 (1H, d, J=8.5 Hz, Ar—H), 7.16 (2H, d, J=7.5 Hz, Ar—H), 9.16 (1H, s, NH, $D_2O$ exchg.), 10.62 (1H, s, CONH, $D_2O$ exchg.); $^{13}$C NMR (125 MHz, DMSO-$d_6$): δ=12.0, 30.24, 55.88, 101.15, 105.12, 109.88, 110.04, 111.27, 128.90, 129.34, 129.75, 130.65, 134.31, 153.49, 170.89; MS: m/z=233.11 $[M]^+$, 234.07 $[M+1]^+$; Analysis: $C_{12}H_{15}N_3O_2$ for, calcd. C, 61.79; H, 6.48; N, 18.01%. found C, 61.58; H, 6.46; N, 18.05%.

Data obtained for 4-Chlorobenzohydrazide (Compound 2) are as follows: Color: white; Yield: 20%; M.p.: 148-150° C.; UV Amax (Methanol)=230 nm; $^1$H NMR (500 MHz, DMSO-$d_6$): δ=4.53 (2H, s, $NH_2$, $D_2O$ exchg.), 7.52 (2H, d, J=8.5 Hz, Ar—H), 7.84 (2H, d, J=8.5 Hz, Ar—H), 9.87 (1H, s, CONH, $D_2O$ exchg.); $^{13}$C NMR (125 MHz, DMSO-$d_6$): δ=128.86, 129.32, 132.50, 136.25, 165.29; MS: m/z=170.45 $[M]^+$; Analysis: $C_7H_7N_2OCl$ for, calcd. C, 49.28; H, 4.14; N, 16.42%. found C, 49.37; H, 4.12; N, 16.46%.

To prepare 2-(5-methoxy-2-methyl-1-indol-3yl)-N-[(E)-substituted phenyl methylidine] aceto hydrazide derivatives (Compounds S1-S18), a solution of indol hydrazide (371 mg, 1.0 mmol) in EtOH (15 mL) containing an appropriate substituted benzaldehyde (1.1 mmol) and a catalytic amount of glacial acetic acid was heated under reflux for 3 hours. After cooling, 5 mL of water was added to the mixture and kept in a refrigerator for 12 hours. The product was filtered and washed with water. The solid was recrystallized from ethanol.

For the experimental results described below, healthy male albino rats (200 g-220 g) were used for the study. The animals were kept in standard plastic animal cages in groups of six animals each with 12 hour light and dark cycle at 25±2° C. The rats were fed on standard rat chow and provided water ad libitum. The animals were acclimatized to laboratory conditions for a week prior to experiments. Anti-inflammatory activity of the synthesized compounds S1-S18 was determined by the carrageenan-induced rat paw edema method. The compounds were tested at equimolar oral dose and were compared with the standard drug indomethacin. The tested compounds showed anti-inflammatory activity ranging from 7.35 to 62.69% inhibition after 2 hours and 7.06%-63.69% inhibition after 4 hours, whereas the standard drug indomethacin showed 77.23% inhibition after 2 hours and 76.89% inhibition after 4 hours. Three compounds, namely S14, S7 and S3 containing R=2,4,5-trimethoxyphenyl; R=3,4-dimethoxyphenyl and R=3-nitrophenyl, respectively, were found to be the most potent compounds with significant anti-inflammatory activity compared with the standard drug indomethacin (as shown in Table 1 of FIG. 2).

Anti-inflammatory activity was determined by a carrageenan-induced rat paw edema method. Male rats weighing 200 g were housed in a room with a controlled temperature and 12 hour light/12 hour dark cycle, housed in a specific pathogen free environment, and fed standard rodent chow and given water ad libitum. Each treatment group and vehicle group consisted of six randomly assigned animals. Compounds were administered p.o. suspension. Paw edema was induced by intradermal injection of 50 μL of 1% carrageenan into the sub plantar region of the right hind paw, after one hour of compound administration. The paw volume was measured immediately after dosing and after 2 hours and 3 hours using a plethysmometer. The control group received only the vehicle. Increase in paw edema was compared with that in the control group and percent inhibition was calculated taking the values in the control group as 0% inhibition.

Compounds which exhibited significant anti-inflammatory activity were selected and tested for analgesic activity. Male albino Swiss mice (25 g body weight) were divided into various groups (n=6). Each mouse was initially placed on a hot plate thermostatically maintained at 58° C. The mouse was watched carefully for the time in seconds in which it displayed nociceptive responses exhibited as licking or blowing (fanning) its front paws. This time was considered as the control reaction time. A cut-off time of 60 s was used to avoid damage to the paws. To test the analgesic activity of the compounds, each group of mice was treated with one dose of the test compounds. The reaction time was then retested at 0 hour and 120 min after injection (each animal acted as its own control). The percentage changes in the reaction were then calculated. Compound S14 (R=2,4,5-trimethoxyphenyl) showed maximum analgesic activity (70.27%), followed by S10 (R=3-hydroxyphenyl) (62.50%), S17 (R=2,4,6-trimethoxyphenyl) (61.53%), S3 (R=3-nitrophenyl) (61.36%), S9 (R=4-hydroxyphenyl) (55.81%), and S7 (R=3,4-dimethoxyphenyl) (47.72%). It is evident from the analgesic activity that three compounds, namely S14, S3 and S7, showed the highest anti-inflammatory activity also showed significant analgesic activity (as shown in Table 2 of FIG. 3).

The compounds were further screened for their ulcerogenic activity (as shown in Table 3 of FIG. 4). For acute ulcerogenesis testing, albino rats were divided into different groups consisting of six animals in each group. Ulcerogenic activity was evaluated after p.o. administration of test compounds or indomethacin at the dose of 20 mg/kg. Control rats received p.o. administration of vehicle (suspension of 1% methyl cellulose). Food (but not water) was removed 24 hours before administration of the test compounds. After the drug treatment, the rats were fed a normal diet for 17 hours and then sacrificed. The stomach was removed and opened along the greater curvature, washed with distilled water and cleaned gently by dipping in saline. The mucosal damage was examined by means of a magnifying glass. For each stomach, the mucosal damage was assessed according to the following scoring system: 0.5 redness; 1.0 spot ulcers; 1.5 hemorrhagic streaks; 2.0 ulcers <3 but ≤5; 3.0 ulcers >5. All of the compounds were tested at equimolar oral doses. The tested compounds showed a significant reduction in ulcerogenic activity ranging from (0.948±0.17 to 0.00). The maximum reduction in ulcerogenic activity (0.00) was found in S4 (R=2-nitrophenyl), S6 (R=2,4-dichlorophenyl), S11 (R=4-dimethylaminophenyl), S15 (R=2,3,4-trimethoxyphenyl) and S17 (R=2,4,6-trimethoxyphenyl) compared to the standard reference drug indomethacin (0.948±0.21).

It is well known that compounds showing less ulcerogenic activity will also show reduced malondialdehyde (MDA) content in liver and kidney tissues. For determination of lipid peroxidation in the gastric mucosa, after screening for ulcerogenic activity, the gastric mucosa was scraped with two glass slides, weighed (100 mg) and homogenized in 1.8 mL of 1.15% ice cold KCl solution. The homogenate was supplemented with 0.2 mL of 8.1% sodium dodecyl sulfate (SDS), 1.5 mL of acetate buffer (pH 3.5) and 1.5 mL of 0.8% thiobarbituric acid (TBA). The mixture was heated at 95° C. for 60 minutes. After cooling, the reactants were supplemented with 5 mL of a mixture of n-butanol:pyridine (15:1 v/v), shaken vigorously for 1 minute and centrifuged for 10 minutes at 4000 rpm. The supernatant organic layer was taken out and absorbance was measured at 532 nm on a UV spectrophotometer. The results were expressed as nmol MDA/100 mg tissue. Data are expressed as mean±S.E.M., and the student's t-test was applied to determine the significance of the difference between the standard group and rats treated with the test compounds. The lipid peroxidation was measured as nanomoles of MDA content/100 mg of liver and kidney tissue. The standard drug, indomethacin, showed the highest lipid peroxidation (8.06±0.28) in liver and (6.70±0.20) in kidney tissues. The compounds which showed less ulcerogenic activity also showed decreased values in lipid peroxidation.

The $LD_{50}$ of compound S3 was determined by the Karber method. The $LD_{50}$ of compound S3 was found to be 35 mg/kg. For $LD_{50}$ determination, an observation was made for each mouse for 24 hours and symptoms of toxicity and rate of mortality in each group were noted. At the end of the study period, expired animals were counted for the calculation of $LD_{50}$. The following method was used for the determination of $LD_{50}$: $LD_{50}=LD_{100}-\Sigma\times(a\times b)/n$, where n is the total number of animals in a group, a is the difference between two successive doses of administered extract/substance, b is the average number of dead animals in two successive doses, and $LD_{100}$ is the lethal dose causing 100% death of all test animals.

Three compounds, namely S14, S3 and S7, were found to be highly significant anti-inflammatory and analgesic agents in the order of S14>S3>S7. These compounds were less ulcerogenic than the reference drug indomethacin in the order of S3>S7>S14. Compound S3 (R=3-nitro phenyl) was found to be a potent anti-inflammatory and analgesic agent with significant gastric sparing activity. S3 as a lead compound showed maximum reduction in gastric ulceration and lipid peroxidation.

In gastro-protective experiments, the ulcer control rats, ethanol-induced and indomethacin with ethanol-induced rats, revealed severe mucosal damage with an ulcer index of 7.83±0.33 and 12.34±0.73, respectively. The compound S3 pretreated rats exhibited a significant decrease in ulcer index, namely 2.83±0.87, and less mucosal damage. These results clearly indicate that compound S3 has gastro-protective activity, as shown in Table 4 below. Mucus production by gastric mucosa increased gradually in the experimental rats pretreated with compound S3. Gastric mucus plays crucial role in gastro-protection. The pretreatment with compound S3 significantly augmented the gastro-protective activity, with enhancement of the free mucus when compared to the mucus of ulcer control animals. The mucus was formed from mucin-type glycoprotein. The mucus gel adhering to the gastric mucosal surface defends the epithelium beneath against acid, pepsin and necrotizing agents, such as ethanol and indomethacin. However, it has been found that gastric wall mucus plays a more important role in the defense of the gastric mucosa against aggression of chemical or mechanical factors than the soluble mucus in the lumen of the stomach. Gastric wall mucus coating might be relieved in the repair of the damaged gastric epithelium. Thus, compound S3 has gastro-protective activity against ethanol and indomethacin ethanol induced gastric ulcer by improving mucosal content.

TABLE 4

Ulcer index of compound S3 compared with standard drug indomethacin

| Animal groups | Treatment (5 mL/kg dose) | Ulcer index (mm$^2$) Mean ± SEM |
|---|---|---|
| 1 | Normal Control | 0 |
| 2 | Ulcer ethanol group | 7.83 ± 0.33 |
| 3 | S3 (25.6 mg/kg) | 2.83 ± 0.87 |
| 4 | Indomethacin (25 mg/kg) | 12.34 ± 0.73 |

The ethanol induced ulcer model was used to study gastro-protective activity of compound S3. The rats were grouped into five groups (n=6). Group I and II received saline solution and served as negative-control and ulcer-control, respectively. Group III received compound S3 (25.6 mg/kg) with ethanol orally and served as the experimental drug group. Animals in groups IV received the indomethacin (25 mg/kg bodyweight) with ethanol. After 1 hour, all of the groups, except Group I, received 20 mL/kg of ethanol 95%. The animals were sacrificed 1 hour later under anesthesia and their stomachs were quickly removed for further studies.

Figure 5A:
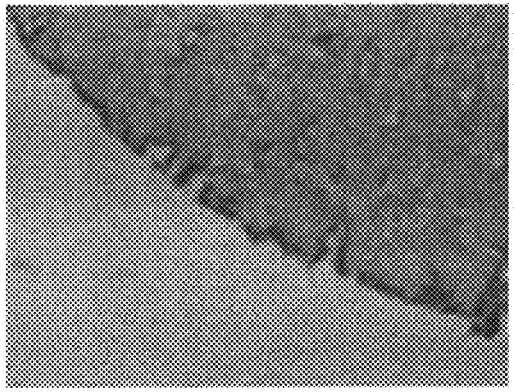
FIG. 5A is a microscope image of an ethanol-induced gastric ulceration, shown with periodic acid-Schiff (PAS) staining, for an untreated control sample.
Figure 5B:
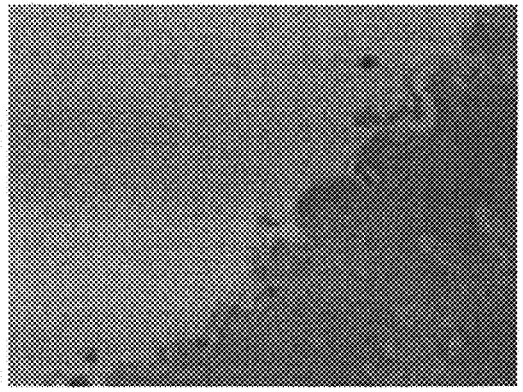
FIG. 5B is a microscope image of an ethanol-induced gastric ulceration, shown with periodic acid-Schiff (PAS) staining, for a sample treated with ethanol.
Figure 5C:
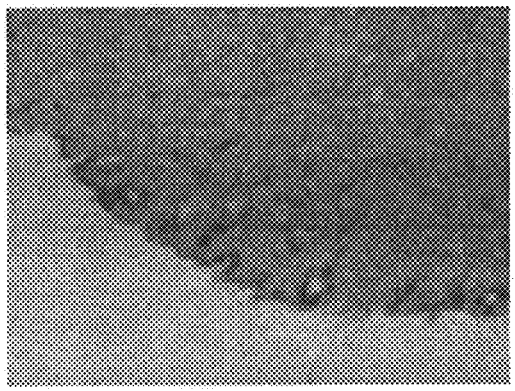
FIG. 5C is a microscope image of an ethanol-induced gastric ulceration, shown with periodic acid-Schiff (PAS) staining, for a sample treated with a cyclooxygenase inhibitor according to the present invention.
Figure 5D:
FIG. 5D is a microscope image of an ethanol-induced gastric ulceration, shown with periodic acid-Schiff (PAS) staining, for a sample treated with indomethacin (25 mg/kg).

Periodic acid-Schiff (PAS) staining was used to observe the glycogen level in control and pretreated animals. Compound S3 pre-treatment resulted in the expansion of a substantially continuous PAS-positive mucous gel layer that lined the entire gastric mucosal surface (observed as a magenta color). However, gastric specimen from ulcer control and indomethacin pretreated groups did not exhibit this magenta staining color of PAS, as shown in FIGS. 5A-5D. Here, FIG. 5A shows the untreated control sample, FIG. 5B shows the ethanol-induced gastric ulceration for a sample treated with ethanol, FIG. 5C shows the sample treated with the present indole derivative anti-inflammatory, analgesic and gastric sparing composition (S3), and FIG. 5D shows the sample treated with indomethacin (25 mg/kg).

Figure 6A:
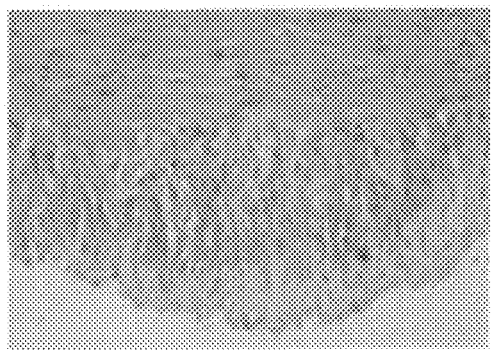
FIG. 6A is a microscope image of a gastric section taken from a control rat specimen, showing intact mucosa.
Figure 6B:
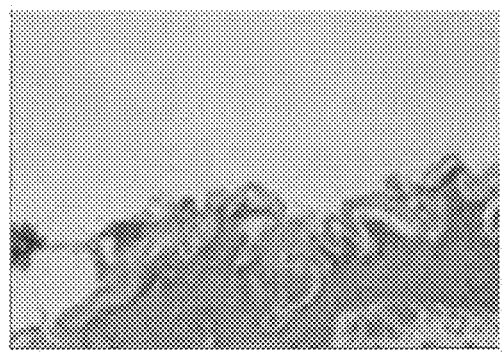
FIG. 6B is a microscope image of a gastric section taken from a rat specimen treated with ethanol.
Figure 6C:
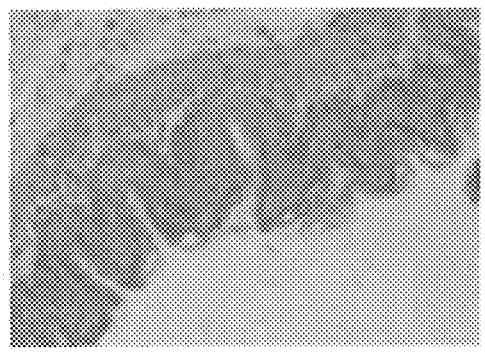
FIG. 6C is a microscope image of a gastric section taken from a rat specimen treated with a cyclooxygenase inhibitor (25.6 mg/kg) according to the present invention and ethanol.
Figure 6D:
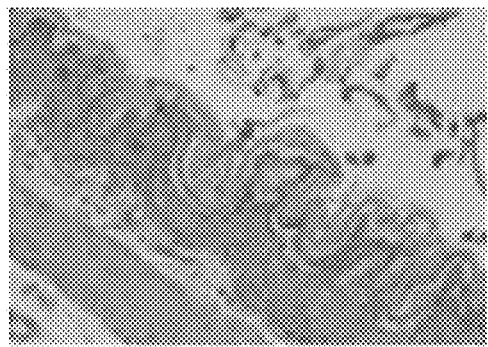
FIG. 6D is a microscope image of a gastric section taken from a rat specimen treated with indomethacin (25 mg/kg) and ethanol.

The ethanol-induced ulcer control shown in FIGS. 5B and 6B exhibits extensive injuries to gastric mucosal cells, and hemorrhagic and necrotic lesions were found to infiltrate deep into the mucosa, causing edema and leukocyte infiltration with inflammation. Furthermore, in animals pretreated with compound S3 (25.6 mg/kg), as shown in FIGS. 5C and 6C, the tissue exhibits a normal glandular pattern with mild inflammation and infiltration of leucocytes in the stomach. The rats pretreated with indomethacin (25 mg/kg), as shown in FIGS. 5D and 6D, demonstrated severe ulceration in comparison with the ethanol induced ulceration. Ethanol-induced gastric ulcers result from several mechanisms, including reduction of gastric mucus and impaired mucosal permeability, and leads to increased leakage of hydrogen ions from the lumen and decreased transluminal membrane potential difference.

With regard to the gross gastric lesion evaluation, the stomach of each rat was opened along the greater arc and washed with saline water to remove gastric contents. Gastric ulcers appear as elongated bands on the gastric mucosa with hemorrhagic lesions being parallel to the long axis of the stomach. The mucosa was assessed for damage under dissecting microscope (1.8×) and a planimeter was used to measure the ulcers area (hemorrhagic lesions). The length and width of each lesion were measured and the sum of the area of all lesions for each stomach was expressed as the ulcer area (mm$^2$).

To determine mucus production of the gastric mucosa, the gastric mucosa of each rat was gently scraped using a glass slide and the mucus obtained was weighed using a precision electronic balance. For the histologic studies, gastric tissues were collected and fixed in 10% formalin after sacrifice. Then, each sample was embedded in paraffin and cut into 5 μm thick slices for morphological and pathological evaluation. Tissue sections were stained with hematoxylin and eosin (H & E) and examined under a light microscope.

Figure 7B:
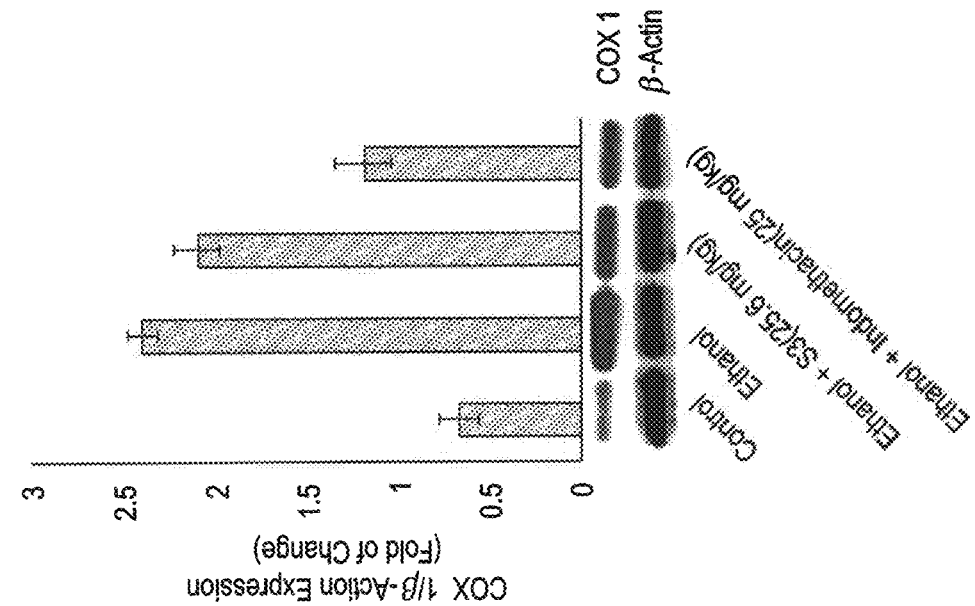
FIG. 7B is a graph showing results of Western blot analysis of COX-1 expression in sample rat gastric mucosa damaged by ethanol, comparing a control sample against samples treated with ethanol, a cyclooxygenase inhibitor (25.6 mg/kg) according to the present invention and ethanol, and indomethacin (25 mg/kg) and ethanol.
Figure 7A:
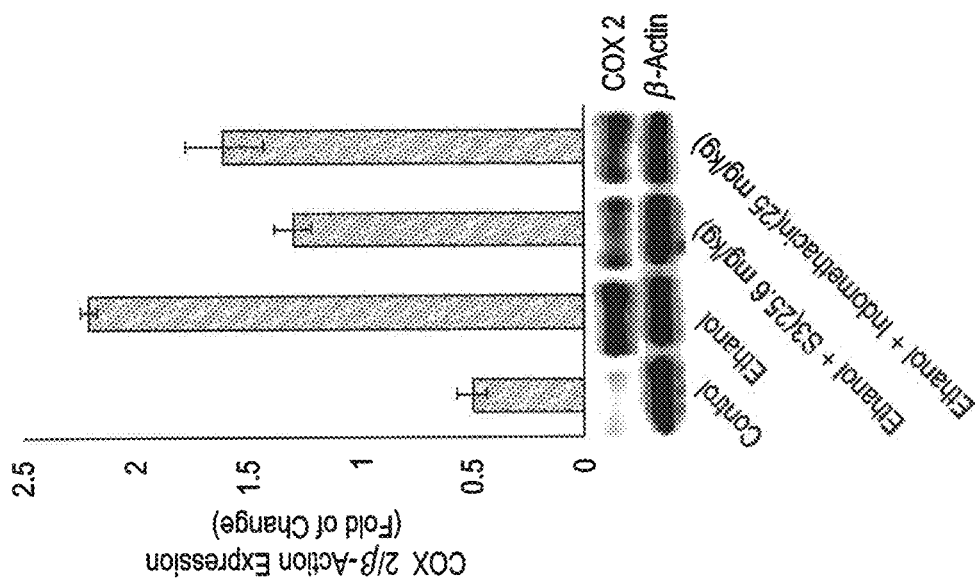
FIG. 7A is a graph showing results of Western blot analysis of COX-2 expression in sample rat gastric mucosa damaged by ethanol, comparing a control sample against samples treated with ethanol, a cyclooxygenase inhibitor (25.6 mg/kg) according to the present invention and ethanol, and indomethacin (25 mg/kg) and ethanol.

A Western blot was performed for COX-1. COX-2 and β-actin protein expression. The compound S3 pretreatment was found to exert gastro-protective action against ethanol-induced gastric damage via attenuating the lesions produced by ethanol, inducing gastric mucus level, decreasing production of COX-1 and COX-2. Indomethacin pretreatment caused gastro-toxicity, as indomethacin is a potent COX-1 inhibitor in the ethanol induced model and a moderate COX-2 inhibitor, as evident by the Western blot results shown in FIG. 7A (COX-2 results) and 7B (COX-1 results). Compound S3 showed potent COX-2 inhibition and weak COX-1 expression. For the Western blot analysis, 20 μg of protein was transferred to PVDF membranes, blocked in 5% skim milk in TBS buffer 1% Tween 20, and then incubated overnight with the COX-1, COX-2 and β-actin, followed by HRP-conjugated anti-rat/rabbit/goat antibodies for 2 hours at 25° C. Bands were visualized with the Luminata Western Chemiluminescent HRP Substrates and densitometric analysis of bands were assessed using LI-COR C-DiGit blot scanners.

The following Examples 1-18 give the spectral data for compounds S1-S18:

EXAMPLE 1

2-(5-methoxy-2-methyl-1H-indol-3-yl)-N-[(E)-phenylmethylidene] acetohydrazide (S1): Yield: 70%; m.p.: 170-172° C.; IR (KBr) cm$^{-1}$: 3412 (NH), 3024 (C—H), 1654 (C=O), 1647 (C=O), 1637 (CN); $^1$H NMR (500 MHz, DMSO-d$_6$): δ=2.37 (3H, s, —CH$_3$), 3.55 (2H, s, CH$_2$), 3.74 (3H, s, —OCH$_3$), 6.65-8.00 (8H, m, Ar—H), 10.62 (1H, s, =CH), 11.26 (1H, s, —NH, D$_2$O exchg.), 11.9 (1H, s, CONH, D$_2$O exchg.); $^{13}$C NMR (125 MHz, DMSO-d$_6$): δ=12.20, 28.28, 55.53, 55.88, 100.77, 104.75, 110.05, 111.30, 127.20, 127.40, 127.61, 129.28, 129.34, 130.03, 130.16, 134.34, 134.81, 153.37, 167.76; MS: m/z=321.37 [M]$^+$; Analysis: for C$_{19}$H$_{19}$N$_3$O$_2$, calcd. C, 71.01; H, 5.96; N, 13.08%. found C, 71.25; H, 5.94; N, 13.11%.

EXAMPLE 2

2-(5-methoxy-2-methyl-1H-indol-3-yl)-N-[(E)-(4-nitrophenyl)methylidene] acetohydrazide (S2): Yield: 75%; m.p.: 220-222° C.; IR (KBr) cm$^{-1}$: 3411 (NH), 3000 (C—H), 1654 (C=O), 1637 (C=O), 1617 (CN); $^1$H NMR (500 MHz, DMSO-d$_6$): δ=2.37 (3H, s, —CH$_3$), 3.58 (2H, s, CH$_2$), 3.74 (3H, s, —OCH$_3$), 6.97-8.26 (7H, m, Ar—H), 10.63 (1H, s, =CH), 11.70 (1H, s, —NH, D$_2$O exchg.), 12.2 (1H, s, —CONH, D$_2$O exchg.); $^{13}$C NMR (125 MHz, DMSO-d$_6$): δ=11.68, 55.06, 100.21, 110.84, 123.99, 124.04, 127.61, 128.02, 128.63, 129.64, 140.49, 145.53; MS: m/z=366.37

[M]⁺; Analysis: for $C_{19}H_{18}N_4O_4$, calcd. C, 62.29; H, 4.95; N, 15.29%. found C, 62.14; H, 4.97; N, 15.25%.

EXAMPLE 3

2-(5-methoxy-2-methyl-1H-indol-3-yl)-N'-[(E)-(3-nitrophenyl)methylidene] acetohydrazide (S3): Yield: 68%; m.p.: 200-202° C.; IR (KBr) cm⁻¹: 3412 (NH), 3237 (C—H), 1654 (C=O), 1640 (C=O), 1617 (C=N); ¹H NMR (500 MHz, DMSO-d₆): δ=2.37 (3H, s, —CH₃), 3.58 (2H, s, CH₂), 3.74 (3H, s, —OCH₃), 6.99-8.57 (7H, m, Ar—H), 10.63 (1H, s, =CH), 11.5 (1H, s, NH, D₂O exchg.), 12.18 (1H, s, —CONH, D₂O exchg.); ¹³C NMR (125 MHz, DMSO-d₆): δ=11.59, 27.92, 55.02, 55.34, 100.27, 103.95, 109.49, 120.72, 123.81, 124.24, 128.57, 129.61, 130.0, 131.73, 132.78, 133.09, 136.05, 140.33, 145.57, 148.14, 152.87, 153.01, 162.27, 167.69; MS: m/z=366.37 [M]+; Analysis: for $C_{19}H_{18}N_4O_4$, calcd. C, 62.29; H, 4.95; N, 15.29%. found C, 62.36; H, 4.93; N, 15.24%.

EXAMPLE 4

2-(5-methoxy-2-methyl-1H-indol-3-yl)-N'-[(E)-(2-nitrophenyl)methylidene] acetohydrazide (S4): Yield: 70%; m.p.: 210-212° C.; IR (KBr) cm⁻¹: 3407 (NH), 3063 (C—H), 1654 (C=O), 1636 (C=O), 1617 (C=N); ¹H NMR (500 MHz, DMSO-d₆): δ=2.37 (3H, s, —CH₃), 3.58 (2H, s, CH₂), 3.74 (3H, s, —OCH₃), 6.98-8.25 (7H, m, Ar—H), 10.63 (1H, s, =CH), 11.90 (1H, s, —NH, D₂O exchg.), 12.10 (1H, s, —CONH, D2O exchg.); ¹³C NMR (125 MHz, DMSO-d₆): δ=11.60, 27.81, 30.56, 54.97, 55.34, 100.15, 103.81, 109.44, 110.84, 124.53, 127.86, 128.13, 129.65, 130.03, 133.42, 134.03, 137.87, 141.48, 143.29, 147.98, 148.21, 152.87; MS: m/z=366.37 [M]+; Analysis: for $C_{19}H_{18}N_4O_4$, calcd. C, 62.29; H, 4.95; N, 15.29%. found C, 62.15; H, 4.97; N, 15.24%.

EXAMPLE 5

N'-[(E)-(4-chlorophenyl)methylidene]-2-(5-methoxy-2-methyl-1H-indol-3-yl)acetohydrazide (S5): Yield: 80%; m.p.: 180-182° C.; IR (KBr) cm⁻¹: 3411 (NH), 3071 (C—H), 1654 (C=O), 1609 (C=O), 1597 (C=N); ¹H NMR (500 MHz, DMSO-d₆): δ=2.36 (3H, s, —CH₃), 3.55 (2H, s, CH₂), 3.74 (3H, s, —OCH₃), 6.60-8.45 (7H, m, Ar—H), 10.63 (1H, s, =CH), 11.3 (1H, s, NH, D₂O exchg.), 12.00 (1H, s, —CONH, D₂O exchg.); ¹³C NMR (125 MHz, DMSO-d₆): δ=11.68, 55.00, 100.00, 110.00, 128.58, 128.74, 128.94, 129.55, 136.64, 146.74, 162.08; MS: m/z=355.81 [M]⁺; Analysis: for $C_{19}H_{18}N_3O_2Cl$, calcd. C, 64.13; H, 5.10; N, 11.81%. found C, 64.33; H, 5.12; N, 11.83%.

EXAMPLE 6

N'-[(E)-(2,4-dichlorophenyl)methylidene]-2-(5-methoxy-2-methyl-1H-indol-3-yl)acetohydrazide (S6): Yield: 65%; m.p.: 238-240° C.; IR (KBr) cm⁻¹: 3411 (NH), 2940 (C—H), 1654 (C=O), 1647 (C=O), 1617 (C=N); ¹H NMR (500 MHz, DMSO-d₆): δ=2.36 (3H, s, —CH₃), 3.59 (2H, s, CH₂), 3.74 (3H, s, —OCH₃), 6.59-8.61 (6H, m, Ar—H), 10.62 (1H, s, =CH), 11.51 (1H, s, —NH, D₂O exchg.), 11.7 (1H, s, —CONH, D₂O exchg.); ¹³C NMR (125 MHz, DMSO-d₆): δ=11.59, 27.84, 30.62, 55.03, 55.34, 100.21, 103.75, 109.41, 110.85, 127.84, 128.73, 129.25, 130.05, 133.48, 134.06, 137.58, 140.96, 152.87, 168.00, 172.00; MS: m/z=390.26 [M]⁺; Analysis: for $C_{19}H_{17}N_3O_2Cl_2$, calcd. C, 58.47; H, 4.35; N, 10.77%. found C, 58.25; H, 4.33; N, 10.74%.

EXAMPLE 7

2-(5-methoxy-2-methyl-1H-indol-3-yl)-N'-[(E)-(3,4-dimethoxyphenyl)methylidene] acetohydrazide (S7): Yield: 70%; m.p.: 210-212° C.; IR (KBr) cm⁻¹: 3299 (NH), 3011 (C—H), 1654 (C=O), 1610 (C=O), 1599 (C=N); ¹H NMR (500 MHz, DMSO-d₆): δ=2.40 (3H, s, —CH₃), 3.70 (2H, s, CH₂), 3.84 (3H, s, —OCH₃), 6.50-8.40 (6H, m, Ar—H), 10.50 (1H, s, =CH), 11.20 (1H, s, —NH, D₂O exchg.), 11.5 (1H, s, —CONH, D₂O exchg.); ¹³C NMR (125 MHz, DMSO-d₆): δ=12.11, 12.23, 55.60, 55.89, 101.08, 121.49, 122.02, 127.57, 143.21, 151.01, 175.00; MS: m/z=381.42 [M]⁺; Analysis: for $C_{21}H_{23}N_3O_4$, calcd. C, 66.13; H, 6.08; N, 11.02%. found C, 66.31; H, 6.10; N, 11.05%.

EXAMPLE 8

2-(5-methoxy-2-methyl-1H-indol-3-yl)-N'-[(E)-(2-methoxyphenyl)methylidene] acetohydrazide (S8): Yield: 60%; m.p.: 220-222° C.; IR (KBr) cm⁻¹: 3315 (NH), 3017 (C—H), 1664 (C=O), 1640 (C=O), 1601 (C=N); ¹H NMR (500 MHz, DMSO-d₆): δ=2.36 (3H, s, —CH₃), 3.56 (2H, s, CH₂), 3.87 (3H, s, —OCH₃), 7.00-8.82 (11H, m, Ar—H), 10.61 (1H, s, =CH), 11.23 (1H, s, NH, D₂O exchg.), 11.92 (1H, s, —CONH, D₂O exchg.); ¹³C NMR (125 MHz, DMSO-d₆): δ=12.19, 55.52, 56.12, 56.17, 63.42, 70.59, 111.29, 112.24, 112.34, 121.24, 122.70, 125.82, 126.00, 129.01, 130.01, 132.14, 137.01, 144.04, 158.28, 162.33; MS: m/z=351.39 [M]⁺; Analysis: for $C_{20}H_{21}N_3O_3$, calcd. C, 68.36; H, 6.02; N, 11.96%. found C, 68.50; H, 6.00; N, 11.93%.

EXAMPLE 9

N-[(E)-(4-hydroxyphenyl)methylidene]-2-(5-methoxy-2-methyl-1H-indol-3-yl)acetohydrazide (S9): Yield: 70%; m.p.: 230-232° C.; IR (KBr) cm⁻¹: 3411 (NH), 3000 (C—H), 1654 (C=O), 1630 (C=O), 1609 (C=N); ¹H NMR (500 MHz, DMSO-d₆): δ=2.37 (3H, s, —CH₃), 3.58 (2H, s, CH₂), 3.75 (3H, s, —OCH₃), 6.59-8.36 (7H, m, Ar—H), 9.88 (1H, s, OH, D₂O exchg.), 10.60 (1H, s, =CH), 11.0 (1H, s, —CONH, D₂O exchg.), 11.73 (1H, s, —NH, D₂O exchg.); ¹³C NMR (125 MHz, DMSO-d₆): δ=12.05, 12,11, 12.20, 28.28, 30.18, 55.56, 55.88, 63.42, 100.86, 101.13, 104.94, 105.09, 109.83, 110.03, 111.18, 111.27, 116.21, 125.79, 128.88, 128.99, 129.14, 129.40, 129.94, 130.55, 134.21, 134.29, 136.86, 143.41, 147.01, 148.96, 153.36, 159.52, 160.00, 162.26, 167.47, 170.73, 172.98; MS: m/z=337.37 [M]⁺; Analysis: for $C_{19}H_{19}N_3O_3$, calcd. C, 67.64; H, 5.68; N, 12.46%. found C, 67.43; H, 5.70; N, 12.43%.

EXAMPLE 10

N'-[(E)-(3-hydroxyphenyl)methylidene]-2-(5-methoxy-2-methyl-1H-indol-3-yl)acetohydrazide (S10): Yield: 60%; m.p.: 145-147° C.; IR (KBr) cm⁻¹: 3413 (NH), 3023 (C—H), 1654 (C=O), 1638 (C=O), 1617 (C=N); ¹H NMR (500 MHz, DMSO-d₆): δ=2.37 (3H, s, —CH₃), 3.57 (2H, s, CH₂), 3.74 (3H, s, —OCH₃), 6.58-8.17 (7H, m, Ar—H), 9.59 (1H, s, OH, D₂O exchg.), 10.62 (1H, s, =CH), 11.21 (1H, s, —NH, D₂O exchg.), 11.39 (1H, s, —CONH, D₂O exchg.); ¹³C NMR (125 MHz, DMSO-d₆): δ=11.60, 27.60, 30.52, 54.98, 55.36, 100.14, 104.05, 109.38, 110.83, 112.49, 117.21, 118.23, 128.55, 129.52, 130.01, 133.88, 135.57, 142.78, 146.22, 152.88, 157.58, 165.00, 172.00; MS: m/z=337.37 [M]+; Analysis for $C_{19}H_{19}N_3O_3$, calcd. C, 67.64; H, 5.68; N, 12.46%. found C, 67.41; H, 5.70; N, 12.42%.

EXAMPLE 11

2-(5-methoxy-2-methyl-1H-indol-3-yl)-N'-{(E)-[4-(dimethylamino) phenyl]methylidene}acetohydrazide (S11): Yield: 65%; m.p.: 200-202° C.; IR (KBr) cm$^{-1}$: 3351 (NH), 2909 (C—H), 1654 (C═O), 1638 (C═O), 1609 (C═N); $^1$H NMR (500 MHz, DMSO-d$_6$): δ=2.37 (3H, s, —CH$_3$), 3.00 (6H, s, 2×NCH$_3$) 3.59 (2H, s, CH$_2$), 3.74 (3H, s, —OCH$_3$), 6.59-8.32 (7H, m, Ar—H), 10.60 (1H, s, ═CH), 10.97 (1H, s, —NH, D$_2$O exchg.), 11.62 (1H, s, —CONH, D$_2$O exchg.); $^{13}$C NMR (125 MHz, DMSO-d$_6$): δ=12.12, 12.22, 100.93, 105.03, 110.00, 111.24, 112.27, 112.31, 122.25, 128.44, 128.70, 128.97, 129.89, 130.56, 143.92, 151.72, 153.36, 172.74; MS: m/z=364.44 [M]+; Analysis: for $C_{21}H_{24}N_4O_2$, calcd. C, 69.21; H, 6.64; N, 15.37%. found C, 69.37; H, 6.66; N, 15.33%.

EXAMPLE 12

2-(5-methoxy-2-methyl-1H-indol-3-yl)-N'-[(E)-(3-methoxyphenyl)methylidene] acetohydrazide (S12): Yield: 65%; m.p.: 195-197° C.; IR (KBr) cm$^{-1}$: 3412 (NH), 3000 (C—H), 1654 (C═O), 1647 (C═O), 1636 (C═N); $^1$H NMR (500 MHz, DMSO-d$_6$): δ=2.37 (3H, s, —CH$_3$), 3.58 (2H, s, CH$_2$), 3.80 (3H, s, —OCH$_3$), 6.59-8.44 (7H, m, Ar—H), 10.67 (1H, s, ═CH), 11.28 (1H, s, —NH, D$_2$O exchg.), 11.46 (1H, s, —CONH, D$_2$O exchg.); $^{13}$C NMR (125 MHz, DMSO-d$_6$): (5=11.60, 27.84, 55.02, 55.35, 100.34, 104.02, 109.38, 110.82, 111.08, 115.63, 119.44, 128.55, 129.54, 130.07, 133.83, 134.02, 135.73, 142.49, 146.12, 152.89, 159.46, 167.39, 172.00; MS: m/z=351.39 [M]+; Analysis: for $C_{20}H_{21}N_3O_3$, calcd. C, 68.36; H, 6.02; N, 11.96%. found C, 68.15; H, 6.00; N, 11.99%.

EXAMPLE 13

N'-[(E)-(4-ethoxyphenyl)methylidene]-2-(5-methoxy-2-methyl-1H-indol-3-yl)acetohydrazide (S13): Yield: 75%; m.p.: 213-215° C.; IR (KBr) cm$^{-1}$: 3322 (NH), 3042 (C—H), 1654 (C═O), 1606 (0=0), 1571 (C═N); $^1$H NMR (500 MHz, DMSO-d$_6$): δ=1.33 (3H, t, J=7.5 Hz, CH$_2$CH$_3$), 2.37 (3H, s, —CH$_3$), 3.57 (2H, s, CH$_2$), 3.74 (3H, s, —OCH$_3$), 4.06 (2H, q, J=7.5 Hz, OCH$_2$), 6.58-8.20 (7H, m, Ar—H), 10.61 (1H, s, ═CH), 11.12 (1H, s, —NH, D$_2$O exchg.), 11.30 (1H, s, —CONH, D$_2$O exchg.); $^{13}$C NMR (125 MHz, DMSO-d$_6$): δ=12.11, 12.20, 15.04, 28.26, 31.05, 55.55, 55.88, 63.70, 100.82, 101.05, 104.66, 104.88, 109.86, 110.03, 111.28, 115.18, 127.26, 128.75, 128.98, 129.29, 129.36, 130.54, 130.63, 134.30, 134.45, 143.00, 146.58, 153.36, 160.27, 167.51, 173.05; MS: m/z=365.42 [M]+; Analysis: for $C_{21}H_{23}N_3O_3$, calcd. C, 69.02; H, 6.34; N, 11.50%. found C, 69.22; H, 6.36; N, 11.53%.

EXAMPLE 14

2-(5-methoxy-2-methyl-1H-indol-3-yl)-N'-[(E)-(2,4,5-trimethoxyphenyl) methylidene]acetohydrazide (S14): Yield: 60%; m.p.: 238-240° C.; IR (KBr) cm$^{-1}$: 3412 (NH), 2943 (C—H), 1654 (C═O), 1638 (C═O), 1617 (C═N); $^1$H NMR (500 MHz, DMSO-d$_6$): δ=2.36 (3H, s, —CH$_3$), 3.51 (2H, s, CH$_2$), 3.78 (12H, s, −4×OCH$_3$), 6.91-8.42 (5H, m, Ar—H), 10.61 (1H, s, ═CH), 11.14 (1H, s, —NH, D$_2$O exchg.), 11.42 (1H, s, —CONH, D$_2$O exchg.); $^{13}$C NMR (125 MHz, DMSO-d$_6$): δ=12.11, 12.20, 55.54, 55.87, 56.43, 56.49, 60.95, 62.19, 100.86, 104.83, 109.15, 109.87, 110.02, 111.29, 120.85, 130.55, 134.30, 138.92, 142.08, 152.86, 153.35, 155.29, 172.98; MS: m/z=411.45 [M]+; Analysis: for $C_{22}H_{25}N_3O_5$, calcd. C, 64.22; H, 6.12; N, 10.21%. found C, 64.35; H, 6.14; N, 10.24%.

EXAMPLE 15

2-(5-methoxy-2-methyl-1H-indol-3-yl)-N'-[(E)-(2,3,4-trimethoxyphenyl) methylidene]acetohydrazide (S15): Yield: 55%; m.p.: 250-252° C.; IR (KBr) cm$^{-1}$: 3310 (NH), 3048 (C—H), 1654 (C═O), 1642 (C═O), 1595 (C═N); $^1$H NMR (500 MHz, DMSO-d$_6$): δ=2.37 (3H, s, —CH$_3$), 3.59 (2H, s, CH$_2$), 184 (12H, s, 4×—OCH$_3$), 6.59-8.74 (5H, m, Ar—H), 10.60 (1H, s, ═CH), 11.08 (1H, s, —NH, D$_2$O exchg.), 11.33 (1H, s, —CONH, D$_2$O exchg.); $^{13}$C NMR (125 MHz, DMSO-d$_6$): δ=12.10, 28.52, 31.14, 55.60, 55.87, 56.26, 56.32, 56.42, 56.95, 98.37, 98.43, 101.16, 104.70, 108.10, 109.88, 111.23, 114.04, 128.98, 129.27, 130.60, 134.20, 138.86, 142.27, 143.65, 152.12, 153.45, 167.32, 172.92; MS: m/z=411.45 [M]+; Analysis: for $C_{22}H_{25}N_3O_5$, calcd. C, 64.22; H, 6.12; N, 10.21%. found C, 64.36; H, 6.10; N, 10.23%.

EXAMPLE 16

2-(5-methoxy-2-methyl-1H-indol-3-yl)-N'-[(E)-(3,4,5-trimethoxyphenyl) methylidene]acetohydrazide (S16): Yield: 58%; m.p.: 233-235° C.; IR (KBr) cm$^{-1}$: 3309 (NH), 3015 (C—H), 1654 (C═O), 1642 (C═O), 1577 (C═N); $^1$H NMR (500 MHz, DMSO-d$_6$): δ=2.37 (3H, s, —CH$_3$), 3.59 (2H, s, CH$_2$), 3.83 (12H, s, 4×—OCH$_3$), 6.97-8.20 (5H, m, Ar—H), 10.61 (1H, s, ═CH), 11.28 (1H, s, —NH, D$_2$O exchg.), 11.40 (1H, s, —CONH, D$_2$O exchg.); $^{13}$C NMR (125 MHz, DMSO-d$_6$): δ=12.11, 12.24, 28.48, 55.60, 55.88, 56.38, 60.56, 60.59, 101.16, 104.64, 109.88, 109.88, 111.26, 130.34, 130.61, 134.26, 139.35, 142.98, 153.61, 173.27; MS: m/z=411.45 [M]+; Analysis: for $C_{22}H_{25}N_3O_5$, calcd. C, 64.22; H, 6.12; N, 10.21%. found C, 64.37; H, 6.10; N, 10.24%.

EXAMPLE 17

2-(5-methoxy-2-methyl-1H-indol-3-yl)-N'-[(E)-(2,4,6-trimethoxyphenyl) methylidene]acetohydrazide (S17): Yield: 55%; m.p.: 230-232° C.; IR (KBr) cm$^{-1}$: 3412 (NH), 3056 (C—H), 1654 (C═O), 1638 (C═O), 1612 (C═N); $^1$H NMR (500 MHz, DMSO-d$_6$): δ=2.37 (3H, s, —CH$_3$), 3.59 (2H, s, CH$_2$), 3.82 (12H, s, 4×—OCH$_3$), 6.57-8.74 (5H, m, Ar—H), 10.61 (1H, s, ═CH), 11.10 (1H, s, NH, D$_2$O exchg.), 11.80 (1H, s, —CONH, D$_2$O exchg.); $^{13}$C NMR (125 MHz, DMSO-d$_6$): δ=12.09, 28.37, 31.12, 55.54, 55.86, 55.88, 56.17, 56.21, 65.38, 98.71, 100.87, 104.72, 106.76, 109.83, 111.28, 115.60, 128.95, 130.56, 132.52, 134.29, 136.36, 144.17, 153.37, 159.44, 162.56, 165.29, 167.39, 172.98; MS: m/z=411.45 [M]+; Analysis: for $C_{22}H_{25}N_3O_5$, calcd. C, 64.22; H, 6.12; N, 10.21%. found C, 64.38; H, 6.13; N, 10.17%.

EXAMPLE 18

2-(5-methoxy-2-methyl-1H-indol-3-yl)-N'-[(E)-(2,4-dimethoxyphenyl) methylidene]acetohydrazide (S18): Yield:

60%; m.p.: 170-172° C.; IR (KBr) cm$^{-1}$: 3413 (NH), 3000 (C—H), 1654 (C=O), 1647 (C=O), 1638 (C=N); $^1$H NMR (500 MHz, DMSO-d$_6$): δ=2.40 (3H, s, —CH$_3$), 3.60 (2H, s, CH$_2$), 3.82 (3H, s, —OCH$_3$), 6.50-8.70 (6H, m, Ar—H), 10.61 (1H, s, =CH), 11.20 (1H, s, NH, D$_2$O exchg.); 11.80 (1H, s, —CONH, D$_2$O exchg.); $^{13}$C NMR (125 MHz, DMSO-d$_6$): δ=11.59, 11.69, 55.00, 55.37, 55.64, 55.68, 98.21, 100.32, 104.44, 106.23, 109.52, 110.78, 115.23, 126.70, 128.36, 129.45, 130.04, 132.00, 133.79, 135.87, 138.39, 143.65, 152.85, 158.85, 162.49, 164.79; MS: m/z=381.42 [M]'; Analysis for C$_{21}$H$_{23}$N$_3$O$_4$, calcd. C, 66.13; H, 6.08; N, 11.02%. found C, 66.34; H, 6.10; N, 11.05%.

It is to be understood that the present invention is not limited to the embodiments described above, but encompasses any and all embodiments within the scope of the following claims.

We claim:

1. A cyclooxygenase inhibitor, comprising a compound having the formula:

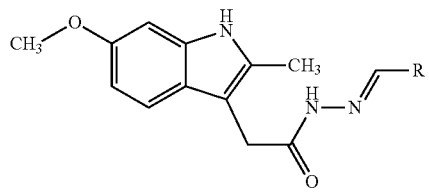

where R is phenyl, nitrophenyl, 2-nitrophenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, dimethylaminophenyl, 3-methoxyphenyl, 4-ethoxyphenyl, 2,4,5-trimethoxyphenyl, 3,4,5-trimethoxyphenyl, 2,4,6-trimethoxyphenyl, and 2,4-dimethoxyphenyl, 3-hydroxyphenyl, 4-dimethylaminophenyl, or 2,3,4-trimethoxyphenyl; or a pharmaceutically acceptable salt thereof.

2. A pharmaceutical composition comprising the cyclooxygenase inhibitor according to claim 1, and a pharmaceutically acceptable carrier.

3. A method for treating inflammation, comprising the step of administering to a patient a therapeutically effective amount of the pharmaceutical composition according to claim 2.

4. A method of making a cylooxygenase inhibitor, comprising the steps of:
refluxing methyl ester of indomethacin and hydrazine hydrate in the presence of absolute ethanol to yield 2-(6-methoxy-2-methyl-1H-indol-3-yl)-acetohydrazide;
refluxing a solution including the 2-(6-methoxy-2-methyl-1H-indol-3-yl)-acetohydrazide and a substituted benzaldehyde in the presence of ethanol and glacial acetic acid to yield a 2-(5-methoxy-2-methyl-1-indol-3yl)-N-[(E)-substituted phenyl methylidine] aceto hydrazide derivative, having the structure:

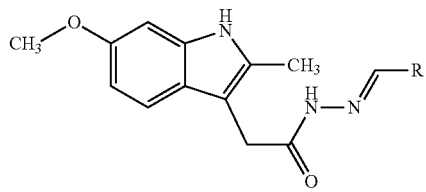

where R is phenyl, nitrophenyl, 2-nitrophenyl, 3-nitrophenyl, 4-nitrophenyl, 4-chlorophenyl, 2,4-dichlorophenyl, 3,4-dimethoxyphenyl, 2-methoxyphenyl, 4-hydroxyphenyl, dimethylaminophenyl, 3-methoxyphenyl, 4-ethoxyphenyl, 2,4,5-trimethoxyphenyl, 3,4,5-trimethoxyphenyl, 2,4,6-trimethoxyphenyl, and 2,4-dimethoxyphenyl, 3-hydroxyphenyl, 4-dimethylaminophenyl, or 2,3,4-trimethoxyphenyl; or a pharmaceutically acceptable salt thereof.

5. The method of making a cylooxygenase inhibitor as recited in claim 4, wherein the step of refluxing the methyl ester of indomethacin and the hydrazine hydrate in the presence of the absolute ethanol comprises refluxing the methyl ester of indomethacin and the hydrazine hydrate in the presence of the absolute ethanol for about 30 hours.

6. The method of making a cylooxygenase inhibitor as recited in claim 5, wherein the solution of 2-(6-methoxy-2-methyl-1H-indol-3-yl)-acetohydrazide and the substituted benzaldehyde are refluxed under heat for 3 hours.

7. The method of making a cylooxygenase inhibitor as recited in claim 5, further comprising the step of recrystallizing the 2-(5-methoxy-2-methyl-1-indol-3yl)-N-[(E)-substituted phenyl methylidine] aceto hydrazide derivative from the ethanol.

* * * * *